(12) United States Patent
Holberg et al.

(10) Patent No.: US 9,297,782 B2
(45) Date of Patent: Mar. 29, 2016

(54) METHOD FOR DIAGNOSING AN ELECTRICAL LEAD TO AN ELECTRODE OF A SENSOR ELEMENT FOR SENSING AT LEAST ONE PROPERTY OF A MEASURED GAS IN A MEASURED GAS SPACE

(71) Applicants: Richard Holberg, Stuttgart (DE); Albrecht Schmidt, Kornwestheim (DE); Christoph Hagner, Korntal Muenchingen (DE)

(72) Inventors: Richard Holberg, Stuttgart (DE); Albrecht Schmidt, Kornwestheim (DE); Christoph Hagner, Korntal Muenchingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 274 days.

(21) Appl. No.: 14/140,143

(22) Filed: Dec. 24, 2013

(65) Prior Publication Data
US 2014/0183060 A1 Jul. 3, 2014

(30) Foreign Application Priority Data
Dec. 27, 2012 (DE) .......................... 10 2012 224 374

(51) Int. Cl.
*G01N 27/417* (2006.01)
(52) U.S. Cl.
CPC .................. *G01N 27/4175* (2013.01)

(58) Field of Classification Search
CPC . G01N 27/409; G01N 27/419; G01R 31/021; F24D 5/00; H01J 1/24
See application file for complete search history.

(56) References Cited

U.S. PATENT DOCUMENTS

2012/0293183 A1* 11/2012 Ledermann ............. F02B 39/16
324/543

OTHER PUBLICATIONS

Robert Bosch GmbH, "Sensoren im Kraftfahrzeug," 1st Edition, pp. 160-165, 2010.

* cited by examiner

*Primary Examiner* — Jennifer Dieterle
(74) *Attorney, Agent, or Firm* — Kenyon & Kenyon LLP

(57) ABSTRACT

A method for diagnosing an electrical lead to an electrode of a sensor element, for sensing at least one property of a measured gas in a measured gas space, in particular for sensing a proportion of a gas component in the measured gas or a temperature of the measured gas, is described. A measured signal indicating an internal resistance of a pump cell of the sensor element is investigated for regularity upon switching on of the control unit. Upon identification of at least one irregularity of the measured signal, a suspected fault in the lead is identified and at least one substitute action is taken. The substitute action is selected from: an application of control to the heating element which is provided for a fault situation, a check of the validity of the measured signal, and a monitoring of the heating element. A sensor apparatus is also described.

15 Claims, 2 Drawing Sheets

METHOD FOR DIAGNOSING AN ELECTRICAL LEAD TO AN ELECTRODE OF A SENSOR ELEMENT FOR SENSING AT LEAST ONE PROPERTY OF A MEASURED GAS IN A MEASURED GAS SPACE

CROSS REFERENCE

The present application claims the benefit under 35 U.S.C. §119 of German Patent Application No. DE 102012224374.7 filed on Dec. 27, 2012, which is expressly incorporated herein by reference in its entirety.

BACKGROUND INFORMATION

A plurality of sensor elements and methods for sensing at least one property of a measured gas in a measured gas space are conventional. Any physical and/or chemical properties of the measured gas can, in principle, be involved, and one or more properties can be sensed. The present invention is described below in particular with reference to a qualitative and/or quantitative sensing of one portion of a gas component of the measured gas, in particular with reference to sensing of an oxygen component in the measured gas part. The oxygen component can be sensed, for example, in the form of a partial pressure and/or in the form of a percentage. Alternatively or additionally, however, other properties of the measured gas can also be sensed, for example the temperature.

Such sensor elements can be configured, for example, as so-called lambda probes, as are described in Konrad Reif (ed.): Sensoren im Kraftfahrzeug (Sensors in motor vehicles), 1st edition 2010, pp. 160-165. Using broadband lambda probes, in particular planar broadband lambda probes, for example, the oxygen concentration in the exhaust gas can be determined over a wide range, and the air-fuel ratio in the combustion chamber can thereby be inferred. The air ratio $\lambda$ describes this air-fuel ratio.

Ceramic sensor elements that are based on the utilization of electrolytic properties of specific solids, i.e., on ion-conduction properties of those solids, are available. These solids can in particular be ceramic solid electrolytes such as, for example, zirconium dioxide ($ZrO_2$), in particular yttrium-stabilized zirconium dioxide (YSZ) and scandium-doped zirconium dioxide (ScSZ), which can contain small additions of aluminum oxide ($Al_2O_3$) and/or silicon oxide ($SiO_2$).

Despite the advantages of the conventional sensor elements and methods for diagnosis, they still have the potential for improvement. For example, an interruption in the lead to virtual ground is usually detected based on the conditions of an implausibly high resistance of the solid electrolyte layer and a pump current of 0 A. This is because in the context of an interruption in the lead to virtual ground, the measurement path for determining the probe's internal resistance is interrupted. The indicated internal resistance is consequently very high even though the probe may be sufficiently hot. The pump current criterion of 0 A results from the fact that the pump current cannot flow off via the lead to virtual ground. Because the system cannot distinguish a cold probe from an interruption in the lead to virtual ground, it is necessary to wait a while after starting before enabling diagnosis. The so-called "pinpointing" effect correspondingly exists. A failed lead to virtual ground and a heating power level fault have the same fault symptoms. In both cases, for example, the measured internal resistance is implausibly high and the pump current is 0 A, so that the two faults can be difficult to distinguish. The system cannot distinguish a cold probe from an interruption in the lead to virtual ground; hence the need for the waiting time (i.e., heating phase) after engine starting before diagnosis can be enabled. Because the measured internal resistance does not correlate with the actual resistance in the event of a fault, the heating regulator requests maximum heating power with no rise in the indicated internal resistance value. Especially in the case of a probe having a high-power heating element, this can result in overheating of the probe. Probe operational readiness is set when the probe temperature exceeds a threshold or the internal probe resistance falls below a threshold. In the event of a fault, the indicated internal probe resistance drifts downward due to thermal effects after a certain time, and a value of approximately 1 kilohm is established. For many types of probe, however, this value is already below the threshold for operational readiness. The result of this is that the lambda controller switches on even though a valid lambda signal is not available due to the failure in the virtual ground lead. This can cause the engine to run roughly.

SUMMARY

An example method for diagnosing an electrical lead to an electrode of an element for sensing at least one property of a measured gas in a measured gas space is proposed, which example method at least largely avoids the disadvantages of conventional methods, and in which example method in particular the detection of a failed virtual ground lead is improved.

The example method according to the present invention for diagnosing an electrical lead to an electrode of a sensor element is embodied to sense at least one property of a measured gas in a measured gas space, in particular to sense a proportion of a gas component in the measured gas or a temperature of the measured gas; the sensor element encompassing a layered structure having at least one solid electrolyte layer, at least two electrodes, and a heating element; the electrodes being interconnected by the solid electrolyte layer in such a way that they form an electrochemical pump cell; the heating element being embodied to heat the electrochemical pump cell in particular to at least a temperature at which the electrochemical pump cell is conductive to ions, in particular to oxygen ions; the electrodes being connected via an electrical connection to a control unit; the electrical connection encompassing the electrical lead; a measured signal indicating an internal resistance of the pump cell being investigated for regularity upon switching on of the control unit; upon identification of at least one irregularity of the measured signal, a suspected fault in the lead being identified and at least one substitute action being taken; the substitute action being selected from: an application of control to the heating element which is provided for a fault situation, a check of the validity of the measured signal, and a monitoring of the heating element.

The electrodes of the pump cell can encompass at least one outer electrode facing toward the measured gas space and at least one inner electrode that is disposed in an electrode cavity and can be impinged upon via a diffusion barrier with gas from the measured gas space, the lead to be diagnosed connecting the inner electrode to the control unit. The inner electrode can be connected in the control unit to a virtual ground and/or can be used as a virtual ground. The sensor element can furthermore encompass a Nernst cell, the Nernst cell having at least one Nernst electrode disposed in the electrode cavity, at least one reference electrode embodied in a reference gas space, and at least one solid electrolyte connecting the Nernst electrode and the reference electrode. The Nernst voltage can be used in the control unit to regulate a pump current of the pump cell. The measured signal indicating the internal resistance of the pump cell can be constituted by a quotient of a pump voltage at the pump cell and a pump current through the pump cell. The pump voltage can be sensed with reference to the electrical lead to be diagnosed. A fault in the electrical lead can be ascertained when, after a predetermined time with the heating element activated, the measured signal exceeds a threshold value and substantially no current is flowing to the electrode. An irregularity of the measured signal can be sensed when the measured signal exceeds or falls below a threshold value within a predetermined time period after the pump current or reference pump current is switched on. An irregularity of the measured signal can be sensed when the measured signal exceeds a threshold value with the control unit switched on. An irregularity of the measured signal can be sensed when the measured signal falls below a threshold value with the control unit switched on. An irregularity of the measured signal can be sensed when the change in the measured signal exceeds a threshold value. A power level of the heating element can be decreased to a predetermined value upon identification of an irregularity. The predetermined value of the heating power level can be a value at which the temperature of the pump cell is held substantially constant at a target temperature. The predetermined value of the heating power level can be a value that is defined as a function of an operating state of the sensor element. The measured signal can be categorized as invalid until completion of the diagnosis. Upon identification of an irregularity of the measured signal, a diagnosis of the heating element can be blocked. The substitute actions can be canceled when a fault in the electrical lead is ascertained. An intact electrical lead can be ascertained when, within a predetermined time with an activated heating element, the measured signal substantially corresponds to a target value and/or when a current to the electrical electrode exceeds a threshold value. The substitute actions can be canceled when an intact electrical lead is ascertained. The predetermined time can be 10 seconds.

A sensor apparatus for sensing at least one property of a measured gas in a measured gas space, in particular for sensing a proportion of a gas component in the measured gas or the temperature of the measured gas, encompasses at least one sensor element and at least one control unit connected via an electrical connection to the sensor element. The sensor apparatus is set up to carry out a method according to one of the above-described possible exemplifying embodiments.

A "diagnosis" of an electrical lead is to be understood in the context of the present invention as monitoring of the electrical lead for a fault in the form of an interruption and/or a short circuit.

A "layered structure" is to be understood in general in the context of the present invention as an element that has at least two layers and/or layer planes arranged one above another. The layers can be distinguishable as a consequence of the manufacture of the layered structure, and/or can be manufactured from different materials and/or starting materials. The layered structure can in particular be configured entirely or partly as a ceramic layered structure.

A "solid electrolyte layer" is to be understood in the context of the present invention as a body or object having electrolytic properties, i.e., having ion-conducting properties. It can in particular be a ceramic solid electrolyte. This also encompasses the raw material of a solid electrolyte and thus the embodiment as a so-called green compact or brown compact that becomes a solid electrolyte only after sintering. The solid electrolyte can in particular be embodied as a solid electrolyte layer or as multiple solid electrolyte layers. A "layer" is to be understood in the context of the present invention as a uniform mass having a planar extension of a certain height, which is located above, below, or between other elements.

An "electrode" is to be understood in general in the context of the present invention as an element that is capable of making contact with the solid electrolyte layer in such a way that a current can be maintained through the solid electrolyte layer and the electrode. The electrode can accordingly encompass an element at which ions can be introduced into the solid electrolyte layer and/or taken out of the solid electrolyte layer. The electrodes typically encompass a noble metal electrode that, for example, can be applied as a metal-ceramic electrode on the solid electrolyte layer or can be otherwise connected to the solid electrolyte layer. Typical electrode materials are platinum cermet electrodes. Other noble metals such as, for example, gold or palladium are, however, also usable in principle.

A "heating element" is to be understood in the context of the present invention as an element that serves to heat the solid electrolyte layer and the electrodes at least to their functional temperature and preferably to their operating temperature. The functional temperature is that temperature at which the solid electrolyte layer becomes conductive to ions, and is equal to approximately 350° C. This is to be distinguished from the operating temperature, which is that temperature at which the sensor element is usually operated, and which is higher than the functional temperature. The operating temperature can be, for example, from 700° C. to 950° C. The heating element can encompass a heating region and at least one supply lead trace. A "heating region" is to be understood in the context of the present invention as that region of the heating element which, in the layered structure, overlaps with at least one electrode in a direction perpendicular to the surface of the sensor element. During operation, the heating region usually heats up more than the supply lead trace. The heating region and/or the supply lead are embodied, for example, as an electrical resistive trace, and heat up as a result of application of an electrical voltage. The heating element can be manufactured, for example, from a platinum cermet.

A "thickness" of a component or element is to be understood in the context of the present invention as a dimension in the direction of the layered structure, and thus perpendicular to the individual layer planes of the layered structure.

A "substitute action" is to be understood in the context of the present invention as an action, deviating from standard operation, for checking a suspected fault and/or for remedying the fault.

A "virtual ground" is to be understood in the context of the present invention as a point in an electrical circuit that exhibits ground potential even though currents are flowing, but is not directly connected to ground. A "ground" is to be understood in general as a conductive body that is ordinarily defined with a potential of 0 volts and that represents the reference potential for all signal voltages and operating voltages. The electrical negative pole of the supply voltage is in most cases simultaneously ground. The positive pole of the supply voltage, as well as all other electrical voltages and electrical signals of an electrical circuit, are referred to the ground potential.

A "reference gas space" is to be understood in the context of the present invention as a space in which a reference gas is present. The reference gas has at least one known property. For example, a proportion of a component of the reference gas is known, for example an oxygen partial pressure. The reference gas space can be embodied, for example, as a reference air conduit. It is possible, however, to embody the reference gas space not as a macroscopic conduit but instead as a so-called "pumped reference," i.e., as an artificial reference in which the reference is pumped, in the form of e.g., oxygen ions, out of the exhaust gas to a reference electrode.

In the context of the present invention the Nernst electrode can be embodied separately from the inner electrode, can be connected to it, or can also be entirely or partly identical to it.

In the context of the present invention the solid electrolyte that connects the Nernst electrode and the reference electrode can be embodied separately from the solid electrolyte of the pump cell or can also be entirely or partly identical to it.

In the context of the present invention the sensor apparatus can be set up to carry out a method as described above. This can be implemented, for example, by a corresponding program-engineering configuration of the control unit, for example of a processor and/or ASIC (application-specific integrated circuit) of the control unit.

A basic idea of the present invention is to detect a suspected lead fault already at an early time after engine start, and to initiate actions in the case of a suspected fault.

The following property of the CJ125 evaluation module of Robert Bosch GmbH, in combination with a continuous lambda probe, are used for suspected fault detection. In the event of a fault involving a failed virtual ground lead, the signal of the measured voltage in proportion to the internal probe resistance exhibits irregularities after the pump current regulator is switched on. Depending on the switch-on strategy for the pump current regulator, the defect is a one-time voltage dip that occurs synchronously with activation of the pump current, or an oscillation in the voltage. The present invention includes investigating the measured voltage in proportion to the internal probe resistance with regard to such a defect, and setting a suspected-fault bit in the event of a defect. The suspected fault is canceled when diagnosis has been completed.

If a suspected fault involving a failed virtual ground lead is present, the heater start diagnosis that proceeds concurrently with the virtual ground lead diagnosis is blocked. In addition, probe operational readiness is withheld. This improves pinpointing between virtual ground diagnosis and heating power level diagnosis. In addition, probe operational readiness and lambda regulation are prevented in the event of a fault.

Suspected fault detection allows a lead interruption to be distinguished, already at an early time after heating startup, from a cold probe. When a fault is suspected, the heating power level is reduced once heater rampup has occurred. Heater regulation is blocked if an internal resistance oscillation is detected. This prevents overheating of the probe. In addition, signal drifting of the internal pump current in the context of an overheated probe, due to reduced insulation resistance, is avoided. Oscillations of the internal resistance signal are also eliminated.

A fault is confirmed if, for an applicable time (e.g., 10 seconds) after the heating phase, the internal resistance is above a threshold value and the pump current is in the 0 A band. The above-described actions may improve fault detection by the fact that disruptive influences on the internal resistance and on the pump current are eliminated.

A test pass is indicated when the internal resistance is within a band around the nominal value for an applicable time after the heating-up phase, or when the pump current departs from the diagnosis band.

BRIEF DESCRIPTION OF THE DRAWINGS

Further optional details and features of the present invention are evident from the description below of preferred exemplifying embodiments that are shown schematically in the Figures.

DETAILED DESCRIPTION OF EXAMPLE EMBODIMENTS

Figure 1:
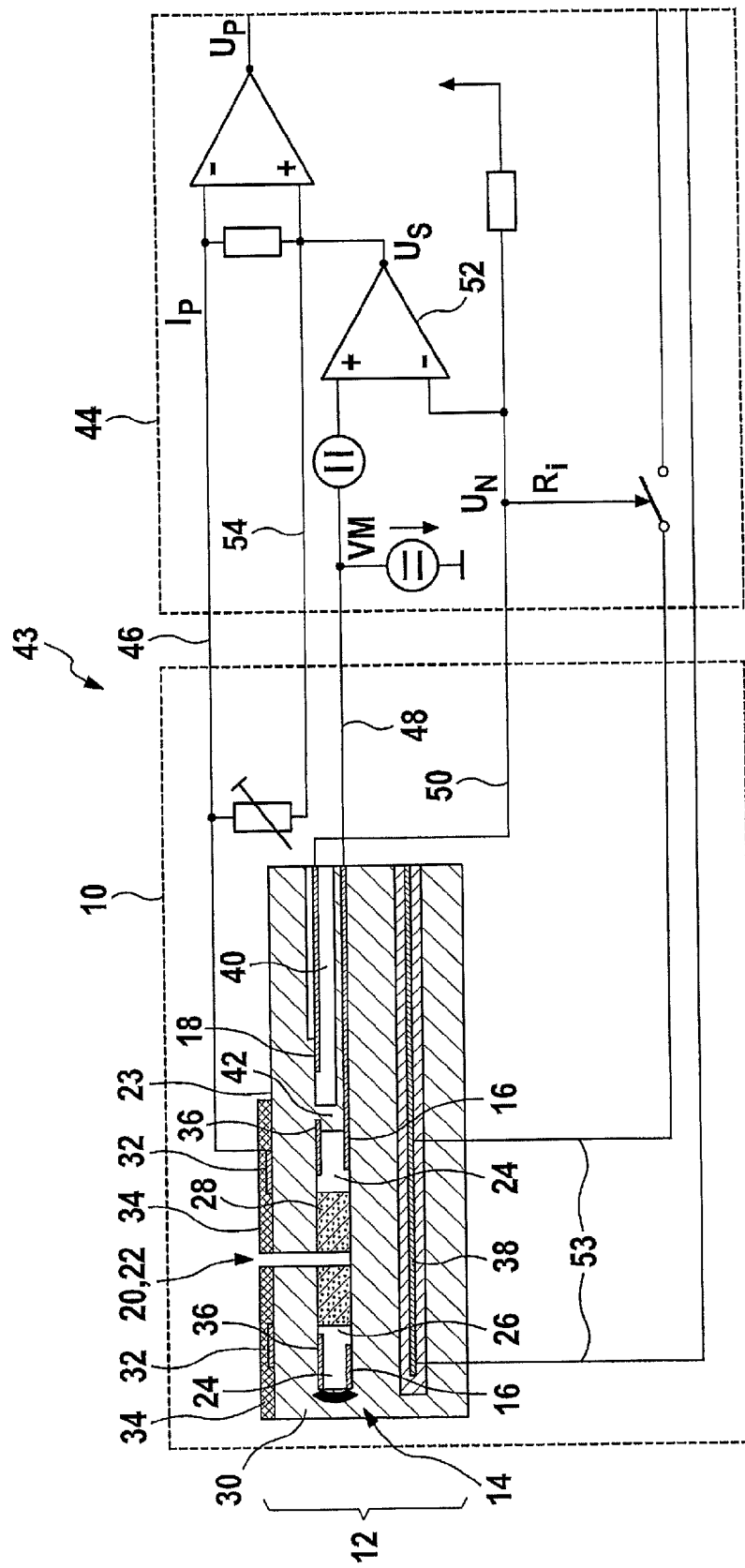
FIG. 1 is a cross-sectional view of an example sensor element according to the present invention and its electrical connections.

Sensor element 10 depicted in FIG. 1 can be used to verify physical and/or chemical properties of a measured gas; one or more properties can be sensed. The present invention is described below in particular with reference to a qualitative and/or quantitative sensing of a gas component of the measured gas, in particular with reference to sensing of an oxygen proportion in the measured gas. The oxygen proportion can be sensed, for example, in the form of a partial pressure and/or in the form of a percentage. In principle, however, other types of gas components can also be sensed, for example nitrogen oxides, hydrocarbons, and/or hydrogen. Alternatively or additionally, however, other properties of the measured gas can also be sensed. The present invention is usable in particular in the sector of motor vehicle engineering, so that the measured gas space can be in particular an exhaust section of an internal combustion engine, and the measured gas can be in particular an exhaust gas.

Sensor element 10 has a layered structure 12 that encompasses a solid electrolyte layer 14 and at least two electrodes 16, 18. Solid electrolyte layer 14 can be made up of multiple solid electrolyte layers, or can encompass multiple solid electrolyte layers. Electrodes 16, 18 are also referred to hereinafter as first electrode 16 and second electrode 18, without indicating any weighting of their significance but merely to distinguish them terminologically. First electrode 16 and second electrode 18 are connected to one another, in particular electrically connected, by solid electrolyte layer 14.

Sensor element 10 further has a gas entry path 20. Gas entry path 20 has a gas entry hole 22 that extends from a surface 23 of solid electrolyte layer 14 facing toward the measured gas space into the interior of layered structure 12. An electrode cavity 24 that surrounds gas entry hole 22, for example annularly, can be provided in solid electrolyte layer 14. Electrode cavity 24 is part of gas entry path 20 and can be in communication with the measured gas space via gas entry hole 22. For example, gas entry hole 22 extends as a cylindrical blind hole, perpendicularly to surface 23 of solid electrolyte layer 14, into the interior of layered structure 12. Electrode cavity 24 is in particular of substantially annular configuration, and is demarcated on three sides by solid electrolyte layer 14. Disposed between gas entry hole 22 and electrode cavity 24 is a conduit 26 that is likewise a constituent of gas entry path 20. Disposed in this conduit 26 is a diffusion barrier 28 that diminishes or even prevents a subsequent flow of gas out of the measured gas space into electrode cavity 24, and enables only diffusion. A limit current of a pump cell 30 can be established by way of this diffusion barrier 28. Pump cell 30 encompasses a third electrode 32, disposed on surface 23 of solid electrolyte layer 14, that can annularly surround gas entry hole 22 and can be separated from the gas space, for example, by a gas-permeable protective layer 34. Third electrode 32 is an outer electrode, facing toward the measured gas space, of pump cell 30. Pump cell 30 further encompasses a fourth electrode 36 that is disposed in electrode cavity 24 and can be impinged upon through diffusion barrier 28 by gas from the measured gas space. Fourth electrode 36 is an inner electrode of pump cell 30. Fourth electrode 36 can likewise be of annular configuration and can be disposed rotationally symmetrically around gas entry hole 22. Third electrode 32 and fourth electrode 36 can be disposed, for example, coaxially with gas entry hole 22. The aforementioned limit current thus represents a current flow between third electrode 32 and fourth electrode 36 via solid electrolyte layer 14. A heating element 38 is disposed in layered structure 12 in the continuation of the extension direction of gas entry hole 22. Heating element 38 is set up to heat pump cell 30, in particular to a temperature at which pump cell 30 is conductive to ions, in particular oxygen ions, for example to 750° C. to 900° C.

Layered structure 12 further encompasses a reference gas conduit 40. Reference gas conduit 40 extends, perpendicularly to an extension direction of gas entry hole 22, into the interior of solid electrolyte layer 14. As mentioned above, gas entry hole 22 is embodied cylindrically, so that the extension direction of gas entry hole 22 proceeds parallel to a cylinder axis of gas entry hole 22. In this case reference gas conduit 40 extends perpendicularly to the cylinder axis of gas entry hole 22. Reference gas conduit 40 can extend, for example, parallel to conduit 26. Viewed in the direction of the cylinder axis of gas entry hole 22, reference gas conduit 40 is located substantially at the same axial height as the end of gas entry hole 22 in the interior of solid electrolyte layer 14. Reference gas conduit 40 can also be disposed along an imaginary extension of gas entry hole 22, and thus farther in the interior of solid electrolyte layer 14. Reference gas conduit 40 can be embodied as a macroscopic reference air conduit in which air having a known property, for example an oxygen partial pressure, is present. Reference gas conduit 40 can alternatively be embodied not as a macroscopic conduit but instead as a pumped reference, i.e., as an artificial reference.

First electrode 16 is disposed in electrode cavity 24. First electrode 16 is located, for example, opposite fourth electrode 36. Second electrode 18 is disposed in reference gas conduit 40. First electrode 16, second electrode 18, and the part of solid electrolyte layer 14 between first electrode 16 and second electrode 18 form an electrochemical cell, for example a Nernst cell 42. First electrode 16 is a Nernst electrode of Nernst cell 42. First electrode 16 can be embodied separately from fourth electrode 36, can be connected to fourth electrode 36, or can be partly identical to fourth electrode 36. In the exemplifying embodiment shown in FIG. 1, first electrode 16 is coupled to fourth electrode 36 via the solid electrolyte layer. Second electrode 18 is a reference electrode of Nernst cell 42. Solid electrolyte layer 14, which is identical to the solid electrolyte of pump cell 30, connects first electrode 16 and second electrode 18. An embodiment in which a solid electrolyte is embodied separately from the solid electrolyte of pump cell 30 is likewise alternatively possible.

Using pump cell 30, for example, a pump current $I_P$ through pump cell 30 can be established in such a way that the condition $\lambda=1$, or another known composition, exists in electrode cavity 24. This composition is in turn sensed by Nernst cell 42 by the fact that a Nernst voltage $U_N$ is measured between first electrode 16 and second electrode 18. Because a known gas composition is present in reference gas conduit 40, the composition in electrode cavity 24 can be inferred based on the measured voltage. The details of the electrical connections of electrodes 16, 18, 32, 36 are described in more detail below.

As shown in FIG. 1, a sensor apparatus 43 encompasses sensor element 10 and a control unit 44. Sensor element 10 is connected to control unit 44 via at least one electrical lead. More precisely, third electrode 32, which is the outer electrode of pump cell 30 facing toward the measured gas space, is connected via an electrical lead 46 to control unit 44. Fourth electrode 36, which is the inner electrode of pump cell 30, is at the same potential as first electrode 16 that is the Nernst electrode of Nernst cell 42, and is connected via an electrical lead 48 to control unit 44. Fourth electrode 36 can be connected in control unit 44 to a virtual ground VM and/or can be used as a virtual ground VM. Virtual ground VM is connected to a non-inverting input of an amplifier 52. The Nernst voltage $U_N$ established between second electrode 18 and fourth electrode 36 is applied to an inverting input of amplifier 52. The voltage that can be picked off between the output of amplifier 52 and lead 46 is the probe voltage $U_S$, and is proportional to a pump current $I_P$ of pump cell 30. In the example shown, fourth electrode 36 is used as virtual ground VM. Second electrode 18, which is the reference electrode of Nernst cell 42, is connected via an electrical lead 50 to control unit 44. Heating element 38 is likewise connected via electrical leads 53 to control unit 44. Also provided is a balancing lead 54 that is connected to lead 46. The voltage that can be picked off between virtual ground VM and lead 46 is the pump voltage $U_P$ and is proportional to an internal resistance $R_i$ of pump cell 30. In control unit 44, the Nernst voltage $U_N$ is used to regulate the pump current $I_P$. A measured signal that indicates an internal resistance $R_i$ of pump cell 30 can be constituted by a quotient of the pump voltage $U_P$ at pump cell 30 and the pump current $I_P$ through pump cell 30. As discussed above, the pump voltage $U_P$ is sensed with reference to lead 48 that is to be diagnosed. A knowledge of the internal resistance $R_i$ is used to regulate the temperature of sensor element 10. For this purpose, heating element 38 is connected via electrical leads 55 to control unit 44.

The example method according to the present invention for diagnosing an electrical lead will now be described in detail. The example method can be carried out by sensor apparatus 43. Second apparatus 43 carries out the method by way of a corresponding program-engineering configuration of control unit 44, for example of a processor and/or ASIC of control unit 44. The lead to be diagnosed is lead 48 that connects fourth electrode 36 or first electrode 16 to control unit 44. When control unit 44 is in the switched-on state, the measured signal indicating the internal resistance $R_i$ is investigated for regularity.

Figure 2:
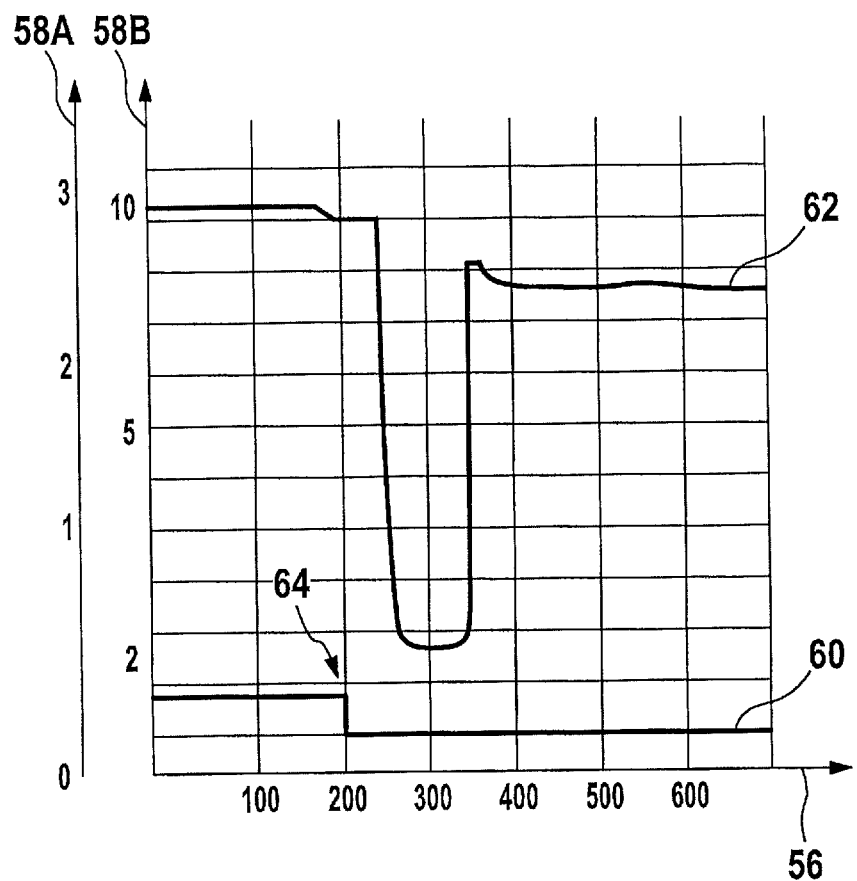
FIG. 2 shows an example of a curve of the control application signal for the pump current and of the measured signal indicating the internal resistance.

FIG. 2 is a diagram in which time in seconds is plotted on X axis 56. The control activation signal for the pump current $I_P$, which follows an inverted logic, is plotted on Y axis 58A, and the measured signal (in V) indicating the internal resistance $R_i$ is plotted on Y axis 58B. Curve 60 indicates the change over time in the control activation signal for the pump current $I_P$, and curve 62 indicates the change over time in the measured signal indicating the internal resistance $R_i$. Be it noted that Y axes 58A and 58B show merely exemplifying values, which can vary depending on the particular control application strategy and switch-on strategy of sensor element 10. The exact values of Y axes 58A and 58B therefore serve merely to explain the present invention, but are not to be construed as a limitation. The exact values of the respective Y axes 58A and 58B thus serve only for relative differentiation among the signal orders of magnitude, but are not to be viewed as correlative or absolute. Only the change over time in curves 60, 62 is relevant for the present invention. Upon identification of at least one irregularity of the measured signal indicating the internal resistance $R_i$, a suspected fault of lead 48 is identified and at least one substitute action is taken. The substitute action can be selected from an application of control, provided for a fault situation, to heating element 38; a check of the validity of the measured signal; and a monitoring of heating element 38. FIG. 2 shows the switching on of control unit 44 and of the pump current $I_P$ at time 64.

Curve 60 therefore shows an instantaneous drop in the control application signal for the pump current $I_P$ at time 64. Synchronously with the switching on of the pump current regulator of control unit 44, the measured signal indicating the internal resistance $R_i$ exhibits irregularities. Depending on the switch-on strategy for the pump current regulator of control unit 44, the irregularities are a one-time voltage dip (as depicted in FIG. 2), or an oscillation of the measured signal indicating the internal resistance $R_i$. An irregularity of the measured signal indicating the internal resistance $R_i$ is sensed when the measured signal exceeds a threshold value within a predetermined time period after control unit 44 is switched on. The predetermined time period can be, for example, 50 ms. The threshold value can be, for example 0.2 V/ms or the internal resistance $R_i$ calculated therefrom in that time period. Alternatively, with other embodiments of lambda probes, an irregularity of the measured signal can be sensed when the measured signal falls below a threshold value within a predetermined time period after control unit 44 is switched on. It is alternatively or additionally possible for an irregularity of the measured signal to be sensed when the measured signal exceeds a threshold value while control unit 44 is switched on. Alternatively, an irregularity of the measured signal can be sensed when the measured signal falls below a threshold value while control unit 44 is switched on.

If an irregularity is ascertained, as depicted by way of example in FIG. 2 as a one-time voltage dip, a suspected-fault bit is set and substitute actions are taken. The suspected fault and substitute actions are canceled only when the complete diagnosis has been carried out. In the case of a suspected fault in the form of an identification of an irregularity of the measured signal, a diagnosis of heating element 38 is blocked. Diagnosis of heating element 38 is usually carried out concurrently with diagnosis of lead 48.

Furthermore, probe operational readiness is withheld. In other words, once the so-called heater ramp-up has elapsed, i.e., the change in temperature or in the electrical voltage applied to heating element 38 over the time for heating the heating element 38, the heating power level is reduced. Upon identification of an irregularity of the measured signal, regulation of heating element 38 is blocked. These substitute actions improve so-called "pinpointing" between the diagnosis of lead 48 and diagnosis of the heating power level. In addition, operational readiness of sensor apparatus 43 and/or of the lambda regulation system is prevented in the event of a fault.

Upon identification of an irregularity of the measured signal, for example, a power level of heating element 38 is decreased to a predetermined value. The predetermined value of the heating power level is a value at which the temperature of pump cell 30 is held substantially constant at a target temperature. The target temperature is, for example, the operating temperature, and can be from 700° C. to 950° C., for example 850° C. The predetermined value of the heating power level is a value that is defined as a function of an operating state of sensor element 10. If pump cell 30 is already hot, the predetermined value can therefore be lower than a value for a cold pump cell 30. This prevents overheating of sensor element 10. In addition, signal drifting of the pump current $I_P$ in the context of an overheated sensor element 10, due to reduced insulation resistance, can be avoided. Oscillations in the measured signal are furthermore eliminated.

A fault in electrical lead 48 is confirmed or ascertained when, after a predetermined time with heating element 38 activated, the measured signal exceeds a threshold value and substantially no current flows to third electrode 32, i.e., the pump current $I_P$ has a value of 0 A. The predetermined time period is, for example, 10 seconds. The actions described above relating to the regulation of heating element 38 and blocking thereof improve fault detection by the fact that disruptive influences on the measured signal and on the pump current $I_P$ are eliminated. The threshold value for the measured signal is an implausibly high value for the internal resistance $R_i$. This is because in the context of an interruption of lead 48, the measurement path for determining the internal resistance $R_i$ is also interrupted. The indicated internal resistance $R_i$ is consequently very high, even though sensor element 10 may be sufficiently hot for solid electrolyte 14 to be conductive. The criterion of 0 A for the pump current $I_P$ results from the fact that the pump current $I_P$ cannot flow off via lead 48. The measured signal is categorized as invalid until the diagnosis is complete. The substitute actions are canceled when a fault in electrical lead 48 is ascertained as described above.

An intact electrical lead 48 is ascertained or identified when, after a predetermined time (e.g., 10 seconds) with heating element 38 activated, the measured signal substantially corresponds to a target value and/or when a current to third electrode 32 exceeds a threshold value, i.e. the pump current >0 A. In other words, a test pass is indicated when the internal resistance $R_i$ after the heating phase is in a band around the rated value for an applicable time, or when the pump current $I_P$ departs from the diagnosis band. The substitute actions are canceled when an intact electrical lead 48 is ascertained.

What is claimed is:

1. A method for diagnosing an electrical lead to an electrode of a sensor element to sense at least one property of a measured gas in a measured gas space, the sensor element including a layered structure having at least one solid electrolyte layer, at least two electrodes, and a heating element, the electrodes being interconnected by the solid electrolyte layer to form an electrochemical pump cell, the heating element being embodied to heat the electrochemical pump cell, the electrodes being connected via an electrical connection to a control unit, the electrical connection encompassing the electrical lead, the method comprising:

checking for regularity a measured signal indicating an internal resistance of the pump cell upon switching on of the control unit; and identifying a suspected fault in the lead, and taking at least one substitute action upon identification of at least one irregularity of the measured signal, the substitute action being selected from: an application of control to the heating element which is provided for a fault situation, a check of the validity of the measured signal, and a monitoring of the heating element.

2. The method as recited in claim 1, wherein the electrodes of the pump cell including at least one outer electrode facing toward the measured gas space and at least one inner electrode that is disposed in an electrode cavity and can be impinged upon via a diffusion barrier with gas from the measured gas space, the lead to be diagnosed connecting the inner electrode to the control unit.

3. The method as recited in claim 2, wherein the inner electrode is one of: i) connected in the control unit to a virtual ground, and ii) is used as a virtual ground.

4. The method as recited in claim 1, wherein the measured signal indicating the internal resistance of the pump cell being constituted by a quotient of a pump voltage at the pump cell and a pump current through the pump cell.

5. The method as recited in claim 1, wherein a fault in the electrical lead is ascertained when, after a predetermined time with the heating element activated, the measured signal exceeds a threshold value and substantially no current is flowing to one of the electrodes.

6. The method as recited in claim 1, wherein an irregularity of the measured signal is sensed when the measured signal exceeds or falls below a threshold value within a predetermined time period after the control unit is switched on.

7. The method as recited in claim 1, wherein an irregularity of the measured signal is sensed when the measured signal exceeds or falls below a threshold value with the control unit switched on.

8. The method as recited in claim 1, wherein a power level of the heating element is decreased to a predetermined value upon identification of an irregularity.

9. The method as recited in claim 1, wherein the predetermined value of the heating power level is a value at which the temperature of the pump cell is held substantially constant at a target temperature.

10. The method as recited in claim 9, wherein the predetermined value of the heating power level is a value that is defined as a function of an operating state of the sensor element.

11. The method as recited in claim 1, wherein the measured signal is categorized as invalid until completion of a diagnosis.

12. The method as recited in claim 1, wherein a diagnosis of the heating element is blocked upon identification of an irregularity of the measured signal.

13. The method as recited in claim 1, wherein an intact electrical lead is ascertained at least one of: i) when, after a predetermined time with an activated heating element, the measured signal substantially corresponds to a target value, and ii) when a current to one of the electrodes exceeds a threshold value.

14. The method as recited in claim 13, the substitute actions being canceled when an intact electrical lead is ascertained or when a fault in the electrical lead is ascertained.

15. A sensor apparatus for sensing at least one property of a measured gas in a measured gas space, the sensor apparatus comprising:
    at least one sensor element, the sensor element including a layered structure having at least one solid electrolyte layer, at least two electrodes, and a heating element, the electrodes being interconnected by the solid electrolyte layer to form an electrochemical pump cell, the heating element being embodied to heat the electrochemical pump cell; and
    at least one control unit connected via an electrical connection to the sensor element, the sensor apparatus configured to check for regularity a measured signal indicating an internal resistance of the pump cell upon switching on of the control unit, and identify a suspected fault in the lead, and take at least one substitute action upon identification of at least one irregularity of the measured signal, the substitute action being selected from: an application of control to the heating element which is provided for a fault situation, a check of the validity of the measured signal, and a monitoring of the heating element.

* * * * *